US007490506B2

(12) United States Patent
Chaintreau et al.

(10) Patent No.: US 7,490,506 B2
(45) Date of Patent: Feb. 17, 2009

(54) MULTIDIMENSIONAL GAS CHROMATOGRAPHY APPARATUS AND ANALYTE TRANSFER PROCEDURE USING A MULTIPLE-COOL STRAND INTERFACE

(75) Inventors: Alain Chaintreau, Plan-Les-Ouates (CH); Frédéric Begnaud, La Roche sur Foron (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/582,919

(22) Filed: Oct. 17, 2006

(65) Prior Publication Data
US 2007/0039375 A1 Feb. 22, 2007

Related U.S. Application Data

(63) Continuation of application No. PCT/IB2005/001311, filed on May 6, 2005.

(30) Foreign Application Priority Data
May 17, 2004 (WO) .................. PCT/IB2004/001589

(51) Int. Cl.
*G01N 1/00* (2006.01)
(52) U.S. Cl. .................... 73/23.41; 73/23.35; 73/23.36; 73/863.12
(58) Field of Classification Search ................. 73/23.25, 73/23.36
See application file for complete search history.

(56) References Cited

U.S. PATENT DOCUMENTS
2005/0139076 A1  6/2005  Ledford, Jr. .................. 96/102

FOREIGN PATENT DOCUMENTS
| WO | WO 98/21574 | 5/1998 |
| WO | WO 03/082427 A1 | 10/2003 |
| WO | WO 03082427 A1 * | 10/2003 |
| WO | WO 2005/111599 A1 | 11/2005 |

OTHER PUBLICATIONS

Marriott, Philip et al., "Cryogenic Solute Manipulation In Gas Chromatography- The Longitudinal Modulation Approach", Trends In Analytical Chemistry, vol. 18, No. 2, pp. 114-125, (1999).*
Begnaud F. et al., XP004820587"Multidimensional Gas Chromatography Using A Double Cool-Strand Interface", Journal Of Chromatography A, vol. 1071,No. 1-2 ,pp. 13-20, (2005).
Marriott P et al., XP-001186437,"Targeted Multidimensional Gas Chromatography Using Microswitching And Cryogenic Modulation",Analytical Chemistry, vol. 75, No. 20, pp. 5532-5538, (2003).

(Continued)

*Primary Examiner*—Hezron Williams
*Assistant Examiner*—Mark Shabman
(74) *Attorney, Agent, or Firm*—Winston & Strawn LLP

(57) ABSTRACT

The invention provides a MDGC apparatus that includes a cryotrapping apparatus capable of cooling at least twice a portion of a chemical sample and provided with a detector device disposed upstream of the cryotrap and allowing identification of the portion of the chemical sample to control the residence time of the latter in the cryotrapping apparatus.

19 Claims, 16 Drawing Sheets

OTHER PUBLICATIONS

Beens et al., XP002337492, "Simple, Non-Moving Modulation Interface For Comprehensive Two-Dimensional GasChromatography", Journal Of Chromatography A, vol. 919, pp. 127-132, (2001).

Marriott P etal., XP004156356 "Cryogenic Solute Manipulation In Gas Chromatography- The Longitudinal Modulation Approach", Trends In Analytical Chemistry, vol. 18, No. 2, pp. 114-125, (1999).

Marriott P et al., XP002337493,"Longitudinally Modulated Cryogenic System. A Generally Applicable Approach To Solute Trapping And Mobilization In Gas Chromatography",Analytical Chemistry, vol. 69, pp. 2582-2588, (1997).

Gorecki et al. XP002337494,"The Evolution Of Comprehensive Two-Dimensional Gas Chromatography (GCxGC)", Journal Of Separation Science, vol. 27, pp. 359-379,(2004).

Kevin A. Krock et al., "Quantitative Aspects Of A Valve-Based, Multi-Stage Multidimensional Gas Chromatography-Infrared Spectroscopy-Mass Spectrometry System", Journal of Chromatography A, vol. 678, pp. 265-277 (1994).

Marriott P et al., "New Operational Modes For Multidimensional And Comprehensive Gas Chromatography By Using Cryogenic Modulation", Journal Of Chromatography A, vol. 866 ,pp. 203-212, (2000).

A. Hagman et al., "Cold Trap/Reinjection Interface for Two-Dimensional Gas Chromatography", Journal Of High Resolution Chromatography & Chromatography Communications, vol. 8, pp. 332-336 (1985).

D. R. Deans et al., "A New Column System for Isothermal Gas Chromatographic Analysis of Light Gases ($H_2$, $O_2$, $N_2$, CO, $CH_4$, $CO_2$, $C_2$, $H_4$, $C_2$, $H_6$ and $C_2$, $H_2$,) Employing a Column Switch Technique", Chromatographia, vol. 4, pp. 279-285 (1971).

D. R. Deans et al., A New Technique for Heart Cutting in Gas Chromatography [1],Research Department, Imperial Chemical Industries Ltd., Heavy Organic Chemicals, pp. 18-22(1967).

Bert M. Gordon, "Comparison of State-of-the-Art Column Switching Techniques in High Resolution Gas Chromatography", Journal Of Chromatographic Science, vol. 23, pp. 1-10, (1985).

Luigi Mondello et al., "Multidimensional Tandem Capillary Gas Chromatography System for the Analysis of Real Complex Samples. Part 1: Development of a Fully Automated Tandem Gas Chromatography System" Journal Of Chromatographic Science, vol. 36, pp. 201-209, (1998).

N. Ragunathan et al.,"Multidimensional Gas Chromatography with Parallel Cryogenic Traps", Analytical Chemistry, vol. 65, No. 20, pp. 1012-1016, (1993).

* cited by examiner

MULTIDIMENSIONAL GAS CHROMATOGRAPHY APPARATUS AND ANALYTE TRANSFER PROCEDURE USING A MULTIPLE-COOL STRAND INTERFACE

CROSS-REFERENCE TO RELATED APPLICATIONS

This application is a continuation of International application PCT/IB2005/001311 filed May 6, 2005, the entire content of which is expressly incorporated herein by reference thereto.

FIELD OF THE INVENTION

The present invention relates to the field of gas chromatographic techniques and their use to detect and/or separate chemical components of complex mixtures of ingredients.

It concerns more particularly a new method of hyphenating gas chromatographic (GC) columns in order to achieve an efficient multidimensional gas chromatography (MDGC) analysis, by using an extremely simple interface based on the cryo-control of the analyte transfer from a first to a second column.

In particular, the present invention relates to a device allowing concentration of chemicals in a carrier phase, gas or fluid, moving along the column interface, thermal modulation being used to alter the rate of flow of the chemicals. Thermal modulation is understood here as including both cooling and heating of the chemical sample, the latter possibly occurring simply by displacing along the interface the cooling source or means after cooling the sample.

The technique is very simple to implement and does not require special column connections or any flow control other than that of the sample carrier means.

BACKGROUND OF THE INVENTION

The present invention relates to on-line GC transfer techniques, meaning methods wherein a group of chromatographic peaks resulting from elution of a complex chemical mixture on a first GC column is transferred automatically to a second GC column in a controlled manner, or eventually to a detection apparatus, namely an olfactometric detection means.

Chromatographic analysis of complex chemical samples is based on the principle that, as the chemical sample flows along a chromatography column, each chemical is separated into a band and possibly detected in the form of a peak, thus allowing separation and identification of each ingredient in the chemical mixture which constitutes the sample. Ideally, each of the chemicals is separated into a discrete band but, in practice, it is common that several ingredients elute at very close times thus producing broad and/or overlapping bands. In an attempt to obtain separate bands and thus complete separation and identification of all the ingredients, such broad or overlapping bands may be resolved by passing them (i.e. the part of the sample eluting from the first column at the time corresponding to the band) through a second column having different chemical or physical characteristics from those of the first column, thus allowing multidimensional resolution of the GC spectrum.

Multidimensional GC is a well-known technique that has been developed early after the invention of gas chromatography. The controlled transfer of analytes from the first to the second column is a critical issue.

There are basically two known ways of carrying out this transfer. In the most recent one, the whole GC profile obtained after elution of the chemical sample fluid stream out of the first column is transferred to the second column, thermal modulation means, namely cryo-control, being provided between the two columns to improve the sensitivity of the peaks eluted out of the second column—we are typically in the realm of the so-called GCxGC or comprehensive gas chromatography field.

In all these prior known methods which use cryo-control of the analyte transfer between columns, the analytes eluting from the first column are continuously trapped and automatically re-injected into a second column at a given frequency, without possible control in the injection rate along the chromatographic run.

Due to the frequency of the transfer pulses (typically 3-5 sec), peaks must elute through the second column in the same time frame as that at which they elute from the first column. As a result, the second column must be a fast-GC column with a smaller inner diameter (typically 0.05-0.10 mm) and considerably shorter length than the first column, otherwise peak overlap may occur.

The fast elution from the second column thus requires a high sampling rate of the detector, which means that conventional detectors such as quadrupole mass spectrometer (MS), infrared (IR) detectors cannot be used.

Moreover, it also prevents optimal detection in applications suited to the fragrance industry for example, where olfactometric evaluation by a perfumer of the peaks as they elute requires high resolution and sufficient time separation between the peaks to allow detection and evaluation by the human nose of the chemical or chemicals of interest.

However, all such known GCxGC interfaces have been designed and automated to sequentially transfer the all chromatogram from the first to the second column and they are not suitable for MDGC.

To specifically re-analyze a given zone of the first chromatogram, a "targeted GC" mode has also been proposed (see for example P. J. Marriott et al., *J.Chromatogr.* 2000, 866, 203-212; P. J. Mariott, WO 98/21574). Using the GCxGC configuration, the target zone is cryo-trapped and transferred into the second column. This still requires a fast-GC analysis to elute the trapped zone in a few seconds in the second dimension, as the rate of retention of peaks eluting before and after the trapped zone remains unchanged. Therefore, the same drawbacks as those previously cited result.

Thus, most of the known multidimensional GC techniques deal with a second method which achieves an on-line "heart-cut", i.e. only some peaks eluted from the first column are transferred to the second one, while others are vented. Such methods fall in the category of the so-called multidimensional gas chromatography (MDGC) techniques.

Alternative techniques, such as the intermediate trapping of analytes in a sorbent and their subsequent desorption in a second column (see for example the articles of K. A. Krok et al. in *J.Chromatogr.* 1994, 678, 265-277 or *Anal.Chem.* 1993, 65, 1012-1016), require far longer analysis times and sophisticated hardware and they do not therefore compete with the method and apparatus which are the object of the present invention.

The so-called "heart-cut" in prior art MDGC can be achieved via two means: with a valve, or with a pneumatic switcher.

A valve is the simplest interfacing as no pressure or flow control is required when two columns of the same diameter are used (see for example L. Mondello et al. in *J.Chromatogr-*

.Sci. 1998, 36, 201-209 or the disclosure in U.S. Pat. No. 5,492,555 to M. R. Strunk et al.).

However, valves can interact with the sample, in particular when the mixtures to be analyzed contain labile components (e.g. sulfur derivatives) susceptible of being degraded by the valve metallic material, namely stainless steel. Other compounds (e.g. carboxylic acids, amines) are prone to adsorption on the stainless steel surface of valves. Such phenomena cause memory effects susceptible of being prejudicial to the analysis (see, for example, B. M. Gordon et al. in *J.Chromatogr. Sci.* 1985, 23, 1-10).

Pneumatic switching has been proposed by D. R. Deans (see for example *Chromatogr.* 1968, 1, 18-21 and 1971, 4, 279-285) which avoids passing analytes through a valve.

However, pneumatic switching requires an accurate flow control of the pressure between the two columns. This must be achieved using a make-up gas and e.g. electronic mass flow controllers. Such sophistication makes the optimization of analytical parameters more complicated and increases instrument cost. Moreover, pneumatic switching may cause some peak broadening.

The use of thermal modulation means, namely a cold trap, has also been proposed to re-focus the heart-cut peak after the pneumatic switching means (A. Hagman; S. Jacobsson in *Journal of High Resolution Chromatography and Chromatography Communications* 1985, 8, 332-336). Then, an additional means to quickly heat and re-inject the trapped peak is required, but again this increases the complexity of the system.

Finally, a "loop modulator", wherein the inlet and outlet of the modulator tube pass in front of a gas jet alternatively supplied with a cold and hot fluid, has also been proposed in International patent application WO 03/82427. The chromatographic column or modulation tube has a loop structure and it allows the measurement of the carrier gas velocity through the modulator tube. It mainly claims to shorten the peak width of modulated peaks.

Although the invention described in this prior art document is based on multi-stage thermal modulation of chemical substances admixed with a carrier gas and flowing through a tube, it still does not provide means to control, in a simple manner, the rate at which successive targeted analytes zones, which are cryo-trapped as they elute from the first column, reach the second column to be eluted there-through, detected and possibly evaluated by a perfumer as they come out of the second column.

In short, none of the prior known chromatographic methods and devices involving automatic transfer of analytes from a first separation column to a second separation column, or to a detection device such as a physical or biological detector, in particular a human nose, comprising a thermal modulator in the analyte transfer line, allows the control of the speed at which a selected peak or group of peaks, which it is desired to completely separate, elutes through the second column or reaches the detector.

The present invention aims at solving this problem.

DESCRIPTION OF THE INVENTION

The present invention relates to a new interface design between chromatographic columns used for multidimensional gas chromatography, and to its specific operation and method of use. Such an interface may also be used with a single column providing advantages even in classical GC analysis.

More particularly, the invention provides an apparatus or device for the analysis and/or detection of chemical components of a chemical sample, comprising conduit means equipped with separation means and temperature modulation means, said conduit means having a receiving port for receiving a chemical sample fluid stream and an outlet port for expelling said chemical sample fluid stream, said ports being in fluid communication with each other to allow movement of the fluid stream from the inlet port towards the outlet port, the temperature modulation means being capable of cooling one or more portions of the conduit means and the chemical sample fluid stream therein, so as to cause at least decrease of the movement of said fluid stream, and of allowing warming up of the chemical sample fluid stream after the cooling so as to resume movement thereof in the conduit means, wherein:
a) the conduit means and the temperature modulation means are arranged in such a way as to allow the chemical sample fluid stream to be cooled at least twice before expulsion thereof through the outlet port;

and
b) detector means are provided up-stream of the first cooling portion of the conduit means so as to allow control of the residence time of the chemical sample fluid stream in the cooled portion or portions of the conduit means.

According to a particularly advantageous embodiment of the invention, the device comprises a loop shaped zone of the conduit means with a double-strand portion equipped with a cryotrap susceptible of being moved along said double-strand to allow thermal modulation of the fluid stream movement of the chemical mixture eluted from a first GC column that one wishes to completely separate in a second GC column. With a single cooling means the chemical sample fluid stream is thus able to pass twice through the cooling zone of the column interface, and the residence time of the sample in the cooling zone, during the two cooling periods, is automatically controllable via means external to the loop, thanks to the presence of the detector located up-stream thereof and which allows detection of the arrival of the peak or peaks of interest and thus remote control of the residual time of the latter, and of successive other targeted peak(s), in the cooling zone of the first, and then the second, strand of the loop.

The device according to the present invention presents the following advantages over prior known devices:
the analytes are only in contact with inert materials, i.e. no transfer through a metallic valve;
there is continuous conduit line from the injector till the detector of the second column, i.e. no carrier gas interruption;
simple or no control of the flow/pressure within the interface;
no dead volumes;
compatible with usual capillary columns (0.15-0.53 mm i. d.), as well as with fast GC columns (0.1 mm i. d. or less) or even packed columns;
low cost;
allows hyphenation with "slow detector" such as quadrupole MS, ion trap detectors, or the human nose;
compatible with simple remote control of the interface by the GC workstation
possibility of using a single chromatographic oven to optimise separation conditions of both first and second column.

The invention further relates to GC chromatographic instruments comprising a device substantially as described above. In fact the device may be associated with any spectroscopic, separation or detection instrument, in particular applicable to analysis of chemical mixtures.

Another object of the invention is a method for detecting and/or evaluating a complex mixture of chemicals, which method comprises the following steps:

a) inserting a chemical sample into a conduit and allowing the chemical sample to travel through the conduit, b) cooling a first portion of the conduit to a predetermined temperature and maintaining the predetermined temperature using thermal modulation means, c) accumulating within the cooled portion of the conduit, for a predetermined period of time, a portion of the chemical sample, thus forming a first concentrated band, d) changing the temperature of the cooled portion of the conduit to allow warming thereof and release the first concentrated band of the chemical sample within the first cooling portion of the conduit, and e) repeating steps c) to d) as many time as desired, to obtain as many subsequent concentrated bands as the number of times these steps are repeated, wherein:

(i) prior to step c) the chemical sample is subjected to detector means susceptible of allowing identification of the portion or portions of the chemical sample to be thus concentrated; and (ii) each concentrated band is subjected to at least a second concentration step via at least a second cooling and warming sequence.

BRIEF DESCRIPTION OF THE FIGURES

FIG. 11a) is a monodimensional GC/MS trace of the analysis of the mixture (column SPB1, 30 m×0.25 mm×1.0 µm), the black line representing the total ion chromatogram and the dotted line representing the selective ion traces of the components.

FIG. 11b) is the chromatogram resulting of the analysis of the same mixture with the cryo-trapping according to the invention, as described in Example 5. The temperature modulation means was automatically operated. The first column was a SPB1, 30 m×0.25 mm×1.0 µm and the second a DB-WAX 30 m×0.25 mm×0.25 µm. The first detector means was a FID whereas a FID and an Ion-trap detector constituted the second detectors means.

DETAILED DESCRIPTION OF THE PREFERRED EMBODIMENTS

Figure 1:
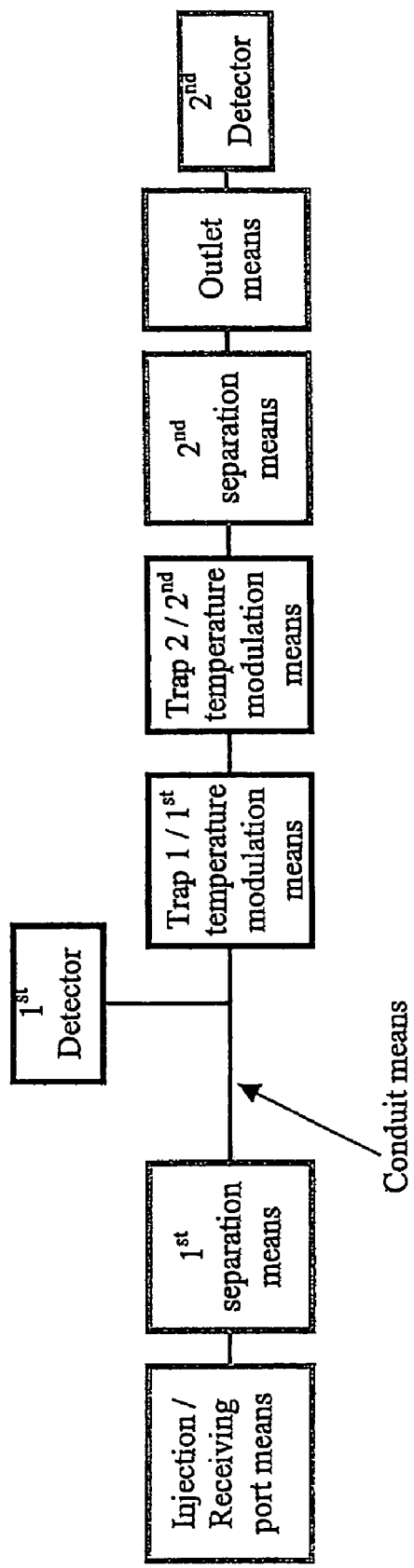
FIG. 1a) is a schematic diagram of an apparatus according to the invention comprising two separation means and two cooling/concentrating means and a detector upstream the first cooling/concentrating means.
FIG. 1b) is a schematic side elevation view of a MDGC apparatus comprising two cooling means arranged in series along the conduit.
Figure 1:
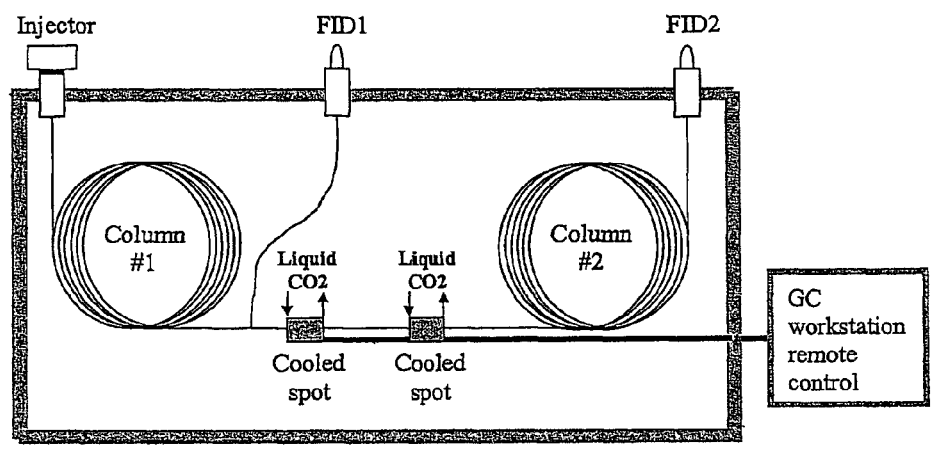

The invention relates to the apparatus or device mentioned earlier. The latter comprises conduit means which may be a tube of any shape adapted to the flow of the fluid stream of the chemical sample. Examples of such conduit means can be found in the prior art and particular reference is made here to the previously mentioned International patent publication WO 98/21574, the contents of which are hereby included by reference.

As mentioned in the prior art document, the conduit means may be a tube, such as a circular, square or rectangular tube. The tube may be formed in any shape including linear, looped, wound or bent. The tube may be wrapped around a support member or bent over a planer surface.

The conduit may be of any length and dimensions. Where the conduit contains more than one section, each section may be of the same or different lengths. The conduit may be part of a chromatographic column such as for example a capillary gas chromatography column or a fluid column. The typical length of a capillary gas chromatography column may be from 0.5 meters to 100 meters long, or even longer, with inner diameter (i. d.) varying from 0.05 mm to 0.75 mm.

Preferably the conduit is made of stainless steel, glass, fused silica, or other metal or glass-lined metal.

The conduit contains a carrier fluid, a gas, to carry the chemical sample which is to be concentrated from the receiving port to the outlet port. The type of carrier fluid in the tube may depend on the type of chemicals present in the chemical sample. Where the conduit comprises more than one section, the carrier gas in each section may be of different composition and/or velocity.

The conduit may also contain a stationary phase. Where the conduit comprises two or more sections, the stationary phase in each section may be of the same or varied thicknesses. The stationary phase in each section may be of the same or different compositions. Some sections of the conduit may have no coating or stationary phase.

In one embodiment, the conduit comprises three sections, a first separating section, e.g. a GC column, a cooling/concentrating section and a second separating or detecting section, e.g. a GC column or other device capable of discriminating the various ingredients of a chemical sample under analysis and/or evaluation. The first column is contained within a housing which has a variable temperature of between ambient and 400° C. at least. The second column is contained within a housing which also has a variable temperature of between ambient and 400° C. at least. The thermal modulation means, namely cooling means, is located on the concentrating section of the conduit. The control of the temperature variation within the two GC columns may be achieved by means of two separate ovens or via a single oven, as described in the examples. The latter embodiment of the device, i.e. comprising a single oven, is particularly simple and advantageous mode of carrying out the invention, namely when used in combination with a single cryotrap in the concentrating zone of the conduit means.

The chemical sample will typically comprise one or more different types of chemicals or components. The apparatus may concentrate one type of chemical at a time from the chemical sample or it may concentrate several types of chemicals together.

The chemical sample to be cooled and thus concentrated may be in a solid, liquid or gas state.

The chemical sample is injected into the receiving port. The injection means is any device or method currently used in the injection or inlet of chemical mixtures into GC columns.

The introduced sample may be derived from a thermal desorption device or from a head-space gas sampler, whereby volatile compounds enter the conduit over an extended period of time.

The chemical sample to be concentrated may contain any chemical components, including volatile organic and inorganic compounds, pesticides, chemical pollutants, semi-volatile compounds, petroleum products, synthetic organic compounds, drugs and other such compounds which may be suitable for chromatography separation and analysis.

Generally speaking, the chemical sample may be in fact any type of chemical composition normally analyzed, detected or evaluated, or susceptible of being analyzed, detected or evaluated, by conventional gas chromatography.

According to a particularly useful embodiment of the invention, the chemical sample will be a fragrance or flavor composition comprising typical odorants or tastants, i.e. substances which possess odor and/or taste, thus of particular usefulness in the perfume and flavor industry.

As previously mentioned, the apparatus or device of the invention makes it possible to control the speed at which a particular section of the GC spectrum, obtained via elution of the sample through a first column, reaches, and travels through, a second column or reaches a detector, or the nose of an individual carrying out olfactive evaluation of the sample being analyzed. This apparatus provides ideal conditions for what is generally known in the perfumery art as "GC-sniffing" or "GC-olfactrometry", i.e. the detection by a human nose of any odorants eluted out of the single or double column device, so as to allow identification of those which may be of interest from a perfumistic point of view or play a role in odor quality control.

As it will become apparent from the examples presented further on, the presence of the detector after the first column, coupled to the "double concentration" (double-cooling) capability of the apparatus of the invention, makes it possible to obtain an improved separation in time of any overlapping or broadened peaks obtained in the first column and thus facilitate identification by a perfumer or other evaluator of the valuable peaks/ingredients. This results in fact from the possibility to delay at will the arrival of any such overlapping or broadened bands at the second column and/or the perfumer's nose, by controlling, thanks to the detection of the targeted bands immediately after they are eluted from the first column, and the subsequent and independent control of the residence time of each of those bands in each of the at least two cooling zones of the conduit.

This possibility to control at will the residence time in the thermally modulated, namely cooling, concentrating zones of the conduit means, also implies that the second column or separation means, no longer needs to be a fast separation device or GC column, unlike what was the case with the prior art devices comprising cryo-control. Since the residence times of distinct bands in the two or more thermal modulators are separately controllable, it is possible to ensure that any one band shall arrive at the second column, and/or at the nose of the perfumer, after a time which is not automatically dictated by the elution rate of the various bands out of the first column, but which has been adjusted as needed by retaining any subsequent peaks following said one first band in the two or more cooling/concentrating zones for the amount of time required for that first band to completely elute through a conventional GC capillary column, without any overlap of the following peaks.

Typically, the apparatus or device of the invention comprises a means for converting the chemical sample into a gas phase if the chemical sample is not already a gas. Preferably the chemical sample is vaporised after entering the receiving port and before flowing through the conduit.

The detector means provided upstream the first cooling/concentrating zone of the conduit is a means of converting some chemical or physical property of the chemical compound into a measurable electronic response. The detector means is able to detect the chemicals present in the chemical sample fluid stream. The detector means may be of any type appropriate to detect chemicals in the chemical sample or chemicals suspected of being in the chemical sample. Typical examples of detector means which may be used in the present invention include mass spectrometry, any of the known ionisation-type detectors, spectroscopic detectors and the like. Preferably a display means is connected to the detector means. The display means is able to indicate the presence of certain chemicals in the chemical sample. Typical examples of display means which may be used in the present invention include chart recorders, electronic data collection means, electronic integrators or computer acquisition and display means.

The thermal modulation means may be any standard known thermal means. If they are cooling means, they may comprise refrigerants such as for example liquid carbon dioxide, liquid nitrogen or any refrigerated gas. The thermal modulation means may be electrical (thermoelectrical cooling warming) systems such as a Peltier cooling device, where the cooled side of the device is used to cool the separation means.

The thermal modulator may also consist of a cooling and/or warming gas jet or jets as described for example in previously cited International publication WO 2003/82427. Such jet modulation devices can also be moveable along the conduit line.

According to particularly useful embodiments of the invention the thermal modulation means is a cooling means or cryotrap which may be moved relative to the conduit means, manually or automatically. It may be moved manually by an operator or automatically by hydraulic means, magnetic means, mechanical means or electronic means. Movement may be automatic, pre-programmed, computer controlled or the like.

In this embodiment, the cooling means may be moveable in relation to the conduit so as to be capable of cooling any portion of the conduit. The cooling means may be moved relative to the conduit in the direction of the flow of the chemical sample or against the direction of flow of the chemical sample fluid stream. Movement may be interrupted to adjust it to the time separation between the overlapping peaks or bands the movement of which it is desired to delay. Preferably the chemicals in the cooled section are cooled to an extent that they are basically motionless.

Preferably the cooling means can cool the chemical sample to a temperature between −200° C. and 100° C. Preferably the cooling means cools the chemical sample to a temperature of between 50° C. and 150° C. less than the temperature of the chemical sample in the remainder of the conduit.

In this embodiment of the invention, the movement of the chemical sample fluid stream can therefore be controlled via displacement of the cooling means—when the sample resides in the zone or zones cooled by the cooling means, its movement can be severely reduced or entirely stopped for the residence time desired and previously set; displacement of the cooling means in the direction opposed to that of the chemical sample stream flow prior to the cooling will allow/cause warming up of the sample, its movement being then resumed towards the subsequent cooling event or events.

In the even more preferred embodiment of the invention exemplified further on, wherein the concentrating portion of the conduit means assumes the form of a loop, the apparatus of the invention requires a single moveable thermal modulation, namely cooling, means, thus making it particularly simple and cost-efficient.

Of course, the thermal modulation means can also be fixed and capable of alternatively cooling and warming up the sample, or at least letting it warm up, as is described for example in WO 2003/82427.

Other possible modes of carrying out the invention will be apparent to the skilled person familiar with cryo-controlled GC methods, by combining variable possible modes of realizing the conduit means and the thermal modulation means in such a way as to allow cooling, followed by warming up, of the chemical sample fluid stream, and thus reducing/stopping, and then resuming, its movement along the conduit means between the two separations zones, namely two GC columns or possibly a GC column and a human nose.

The cooling means may be held stationary relative to the conduit for any period of time. Typically, a sample may be concentrated for period of some tenths of seconds to a few tens of minutes.

As previously indicated, the apparatus of the invention makes it possible to cool, and allow subsequent warming up of, the chemical sample fluid stream at least twice. This can be achieved by providing one or more thermal modulation means as described above between the two separation zones (i.e. GC columns) of the conduit means.

With reference to FIG. 1a), according to an embodiment of the invention, the apparatus comprises injection means as the receiving port for the chemical sample, a first separation means preceding the first detector means and the concentration zone is provided with at least two cooling traps located prior to the second separation zone.

In this embodiment of the invention, as represented in FIG. 1b), the chemical sample, optionally together with a carrier fluid, is injected in the first separation column and subjected to the detector allowing identification of the portions thereof to be concentrated. The sample travels to the first cooling zone where its movement is retarded, and more preferably stopped, for a period of time prior set via the remote control computer, as a function of the characteristics of the GC spectrum obtained after the first column. The temperature of the first cooled spot is then increased, either by moving the cooling means or through heating thereof, and the sample thus resumes its movement towards the second cooling spot where it is again retained for a pre-determined time, after which it flows through the second column connected to a second detector means. The cooling fluid used in the embodiment represented in FIG. 1 is $CO_2$, but it goes without saying that other cooling means may be used without changing the essential character of the invention. The detector means connected to the outlet port of the second separation means is any appropriate detector such as previously mentioned in the text with regard to the first detector means.

Figure 2:
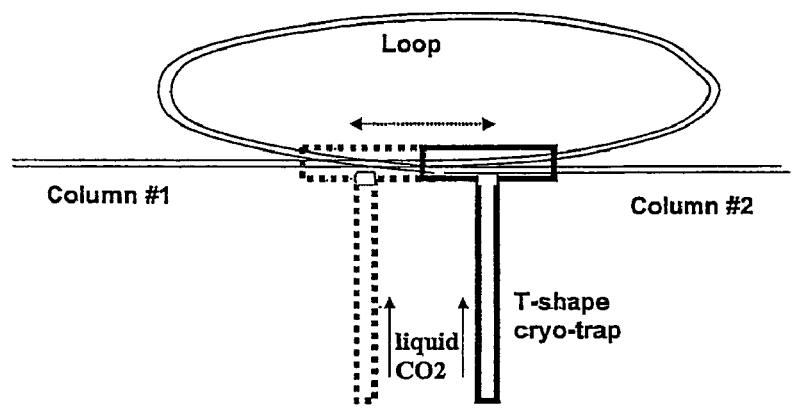
FIG. 2 is a schematic side elevation view of a T-shaped cryotrap which can be manually operated and is arranged so as to be able to cool two portions of the double strand.

According to another, more preferred, embodiment of the apparatus of the invention, represented in FIG. 2, the conduit means comprises a cooling/concentrating zone formed as a double strand loop and the unique thermal modulation means is arranged in the loop so as to provide for cooling of the sample in both strands, at different moments in time. The conduit means is provided with detector means after the first separation zone or GC column, upstream of the first cooling/concentrating zone of the double-strand loop.

Other embodiments of the invention may combine double-stranded loops with further thermal modulation zones provided in series after the sample has travelled the loop section. In general terms, the cooling/concentrating portion of the conduit means may assume any form and length which is convenient to allow maximum flexibility of the control of residence time of the chemical sample in the two or more thermal modulation, namely cryo-modulated, zones.

Figure 3:
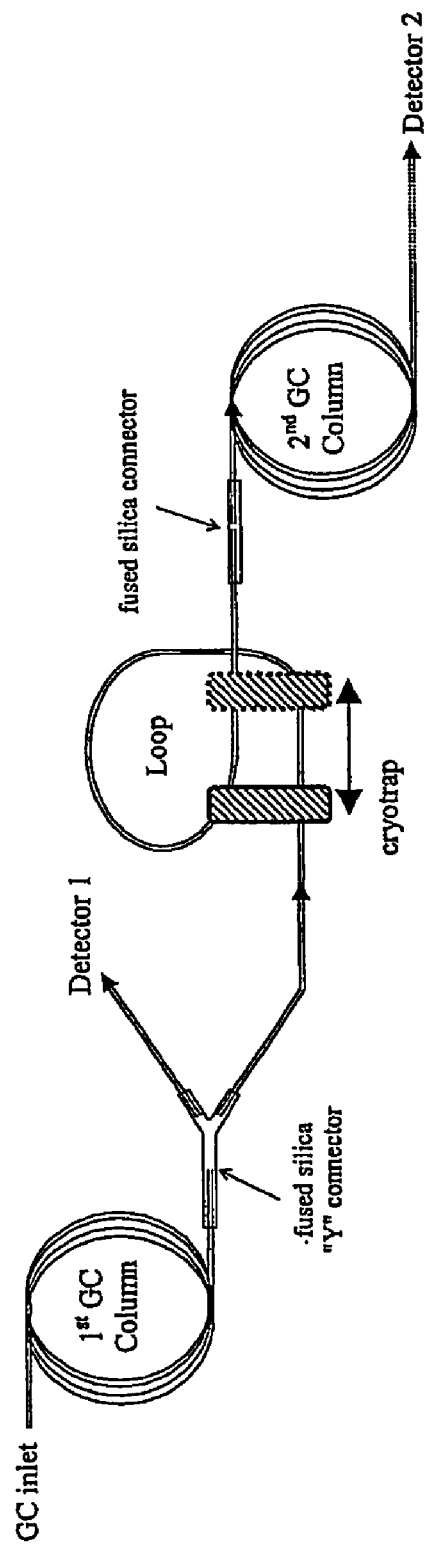
FIG. 3 is a schematic view of a MDGC apparatus comprising a single cooling means disposed on a conduit means comprising a double strand loop portion, with the different connections used between the conduit means and the detectors means.

In the preferred embodiment represented in FIG. 3, the apparatus comprises a conduit consisting of three sections, a first separation section, column 1, a connecting section and a second separation section, column 2. The connecting section is in the form of a loop. A detector means is provided between the first column and the loop which is typically a part of the connecting section. A movable cooling means is provided along the connecting section. The chemical sample is injected into a receiving port and vaporised before flowing along the first separation section. In the first column, the chemicals in the chemical sample are roughly separated into chemical bands. The latter are detected by the detector means to allow detection of the bands prior identified as requiring concentration and further separation in the second column. The chemical sample thus identified, i.e. the targeted peak or band, then flows through the connecting section until it reaches the area of the conduit means subjected to the cooling means. This first chemical band reaches the area of the conduit subjected to the cooling means first. Depending on the temperature of the cooling means the chemical sample subjected to the cooling means is either slowed or stopped in the cooled section, hence concentrating the chemical peaks in the cooled section. Once all of the chemical band from the chemical sample has been stopped or slowed by the cooling means, the cooling means is then moved along the loop to another area. On movement of the cooling means along the conduit, the chemical band which has been slowed or frozen is remobilised by ambient heat or a heating means and begins movement along the loop towards the second strand cooling zone, in this case the second strand of the loop, where its movement is again slowed or stopped, and resumed, as described above. The band then proceeds along the second column. Upon reaching the end of the second column, the concentrated chemical band is expelled from the outlet port in a sharp band which is detected by a detector means and relayed to a display unit.

The invention creates a peak-free zone in the chromatogram for the elution of the target peak(s). Whereas a true "heart-cut" only transfers a (few) peak(s) from the first to the second column, the present invention allows delaying the transfer of analytes between the two columns using a cryogenic trap that cools two strands of a same GC column.

The cryotrap can be e.g. a simple T-shape tube in which two strands of the same capillary column are inserted as is represented in FIG. 2. The motion of the cryotrap can be manually operated and ensured from the oven outside using a rod attached to the trap.

Figure 4:
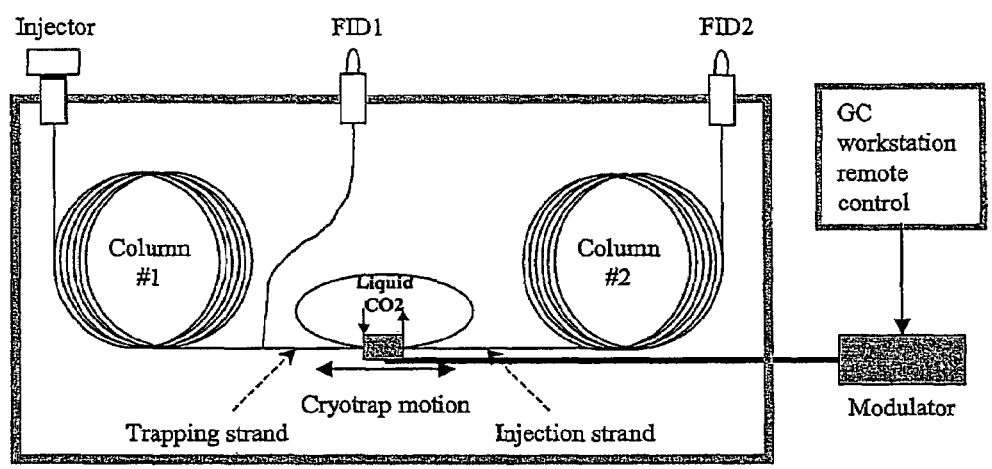
FIG. 4 is a schematic side elevation view of a MDGC apparatus comprising a single cooling means disposed on a conduit means comprising a double strand loop portion.

Preferably however, the cryotrap is operated automatically and remote controlled by the computer of the chromatograph as shown in FIG. 4. Such an automated interface may include in particular LMCS (Longitudinally Modulated Cryogenic System), cold/hot jets, etc., i.e. any type of thermal control proposed as a modulator for comprehensive multidimensional gas chromatography (GCxGC). In contrast to GCxGC, the trapping is not applied at a fixed frequency, but programmed as a function of the retention time of a target peak or group of peaks.

To detect the peak(s) to be trapped, a fraction of the gas flow is split, using a zero dead volume crosspiece, towards a FID after the first column, preferably before the cryotrap.

The zero dead volume crosspiece may also be connected to a pressure gauge, or to a flow or pressure regulator enabling the addition of a make-up gas in the second column if desired, although the invention device dispenses with such components.

Figure 5:
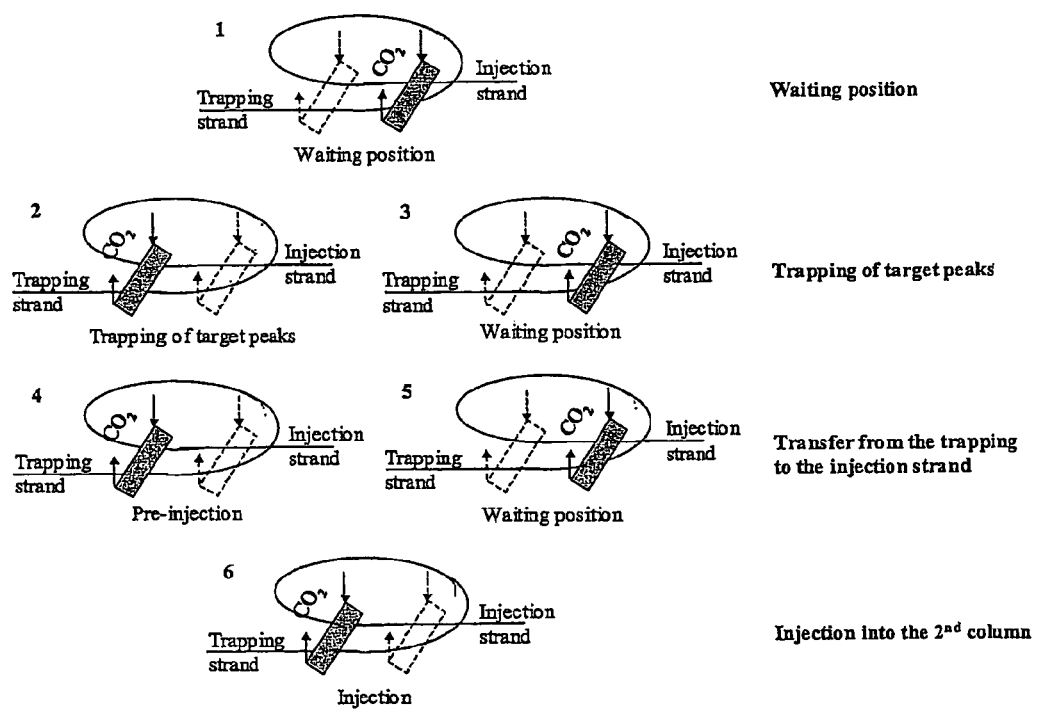
FIG. 5 is a diagram representation of the working principle of double cool strand interface according to the invention. All operating positions are illustrated.

The invention includes the specific operation of the cryotrap to achieve the transfer of the target peak(s) from the first column, into a free zone of the second column. As an example, when a manually operated system (FIG. 2) or a commercially available cryogenic trap (LMCS) is used, this latter allows to stop the elution of analytes in the cold zone. Then, when moving the trap, the cold zone is re-heated by the GC-oven and analytes are re-injected as very narrow peaks. With reference to FIG. 5, the trap motion is remote-controlled by the GC workstation, according to the following sequence:

(a) Waiting position (FIG. 5.1): peaks preceding the target peaks are trapped in the trapping strand.
(b) Trapping of target peaks (FIG. 5.2): the target zone is stopped in the trapping strand while the preceding peaks are transferred in the injection strand.
(c) Back to the waiting position (FIG. 5.3): target peaks are still stopped in the trapping strand. Preceding peaks are ready to be injected in the second column.
(d) Pre-injection (FIG. 5.4): the target zone is transferred from the trapping strand to the injection strand. Preceding peaks are injected in the second column. Following peaks are blocked in the trapping strand.
(e) Back to the waiting position (FIG. 5.5): target peaks are ready to be injected. Following peaks are still blocked in the trapping strand.
(f) Injection (FIG. 5.6): the target zone is injected into the second column. Following peaks are transferred from the trapping strand to the injection strand. They are retained in the injection strand.

The time delays between these steps depend on the retention time of the targeted peaks, on their duration and on the presence of interfering peaks before and after the target zone. Delays are adjustable by the analyst, as a function of the retention time, owing to the external events of the GC workstation.

One of the main advantages of this new interface is its simplicity. It does not require any flow or pressure control and is compatible with usual capillary columns as well as with fast GC columns. The connecting parts used (fused capillary connector) avoid creating dead volumes within the chromatographic system. Moreover, analytes are never in contact with potentially reactive materials such as metallic parts, which is of great importance when analyzing compounds like sulfur containing materials.

In another aspect of the invention there is provided a method of concentrating chemicals in a chemical sample comprising the steps of a) inserting the chemical sample into a conduit and allowing the chemical sample to travel through the conduit;
b) cooling a portion of the conduit to a predetermined temperature and maintaining the predetermined temperature using the thermal modulation means;
c) accumulating within the cooled portion of the conduit for a predetermined period of time a portion of the chemical sample, thus forming a first concentrated band;
d) changing the temperature of the cooled portion of the conduit to allow warming thereof—and release the first concentrated band of the chemical sample within the first cooling portion of the conduit, and e) repeating steps c) to d) as many time as desired, to obtain as many subsequent concentrated bands as the number of times these steps are repeated, wherein:
   (i) prior to step c) the chemical sample is subjected to detector means susceptible of allowing identification of the portion or portions of the chemical sample to be thus concentrated; and
   (ii) each concentrated band is subjected to at least a second concentration step via at least a second cooling and warming sequence.

The chemical sample is carried in a carrier fluid flow through the conduit means.

The device of the invention can be used as part of a multi-dimensional gas chromatograph (MDGC) apparatus to separate and analyze complex mixtures of chemicals or to evaluate the olfactive characteristics of the ingredients thereof.

EXAMPLES

Examples of use of the apparatus will be described hereinafter in a more detailed manner and by reference to the preferred embodiments represented in the Figures.

General Conditions

1. Materials Used

Hyacinth oil was obtained from Quest International (Naarden, Netherlands), jasmin oil from Danisco (Zug, Switzerland) and lavender oil from Firmenich SA (Geneva, Switzerland). Bergamot oil was a commercial test sample. All pure compounds were analytical grade (Purity>97%) except for α-isomethylionone (>95%). α-Ionone, β-ionone, (+/−)-linalool and (−)-linalol were purchased from Fluka (Buchs, Switzerland), α-isomethylionone from Bedoukian (Danbury, USA), tetrahydrolinalool was purchased from BASF AG (Frankfurt, Germany) and Zestover® (2,4-dimethyl-3-cyclohexene-1-carbaldehyde) from Givaudan (Vernier, Switzerland). Nonanal, terpinolene and phenylethanol came from Firmenich SA. Compounds and mixtures were diluted 1:20 (v/v) using ethyl acetate (analysis grade, SDS, Peypin, France) prior to injection.

2. Gas Chromatography

MDGC analyzes were performed using a 6890N gas chromatograph (Agilent Technologies, Wilmington, USA) equipped with two flame ionization detectors (FID, Agilent Technologies) and a longitudinally modulated cryogenic system (LMCS, Everest model unit, Chromatography Concepts, Doncaster, Australia). Two columns with different retention affinities were serially connected via a deactivated silica capillary (0.5 m×0.25 mm i.d., Supelco, Buchs, Switzerland) passing through the LMCS cryotrap. Helium purified with filters for water, oxygen and hydrocarbons was used as carrier gas and delivered at constant pressure. Samples (1 μl) were injected with a 1/50 split. Chromatographic configurations and conditions are summarized in Table 1. All instrumental parameters and data acquisition were controlled via the Galaxie Chromatography Data System software (Varian-JMBS, Fontaine, France).

TABLE 1

Analytical conditions used for the different examples

| Exampl | Product | 1$^{st}$ column/2$^{nd}$ column | Detectors after 1$^{st}$ column/2$^{nd}$ column | Inlet temperature/pressure | Oven temperature program |
|---|---|---|---|---|---|
| 1-2 | Ionones | SPB1, 30 m × 0.25 mm × 1.0 μm, Supelco/DB-WAX 30 m × 0.25 mm × 0.25 μm, J&W Scientific | FID[a]/FID[a] | 250° C./280 kPa | 5 min at 40° C. then 5° C./min to 220° C. 5 min |
| 3 | Jasmine and Hyacinth essential oils | SPB1, 30 m × 0.25 mm × 1.0 μm, Supelco/DB-WAX 30 m × 0.25 mm × 0.25 μm, J&W Scientific | FID[a]/FID[a] | 250° C./280 kPa | 5 min at 40° C. then 5° C./min to 220° C. 5 min |
| 4 | Enantiomers of linalool in bergamot oil | SPB1, 30 m × 0.25 mm × 1.0 μm, Supelco/Megadex DMPβ 10 m × 0.25 mm × 0.25 μm, Mega | FID[a]/FID[a] | 250° C./280 kPa | 90 min at 85° C. then 10° C./min to 150° C. |
| 5-6 | Fragrance model mixture | SPB1, 30 m × 0.25 mm × 1.0 μm, Supelco/DB-WAX 30 m × 0.25 mm × 0.25 μm, J&W Scientific | FID[a]/FID[a] + Ion Trap Detector[b] & FID[a]/FID[a] + Sniff port[c] | 250° C./280 kPa | 5 min at 40° C. then 5° C./min to 220° C. 5 min |
| 8 | Chiral resolution of linalool and linalyl acetate in lavander oil | CP-Sil5CB 30 m × 0.32 mm × 1.0 μm, Chrompack/Megadex DETTBSβ 25 m × 0.25 mm × 0.25 μm, Mega | FID[a]/FID[a] | 250° C./280 kPa | 2 min at 50° C. then 8° C./min to 165° C. 1 min then 25° C./min to 120° C. 8 min then 25° C./min to 50° C. 1 min then 2° C./min to 150° C. 1 min |
| 9 | Olfactive characterization of linalol's enantiomers | Megadex DMPβ 10 m × 0.25 mm × 0.25 μm, Mega/Deactivated capillary 1 m × 0.25 mm, Supelco | FID[a]/Sniff port[c] | 250° C./280 kPa | 15 min at 90° C. then 15° C./min to 180° C. 5 min |

[a] supplied by Agilent Technologies,
[b] supplied by Finnigan Mat,
[c] home made 3. Double Cool Strand Interface The capillary connecting the two columns was wound to form a loop, which strands were passed trough the cryotrap of the LMCS (FIG. 3). The flow exiting the first column was split in two parts owing to a deactivated fused silica "Y" connector. One part was hyphenated to the capillary loop whereas the second one was connected to the first flame ionization detector (FID) to detect the peak to be trapped. The loop outlet was connected to the second column inlet via a glass-coated mini-union capillary connector (SGE, Courtaboeuf, France). The second-column outlet was directly connected to the second FID. When required, this second FID was connected in parallel with an MS or a sniff port (vide infra). The LMCS was monitored by the external events of the workstation, as a function of the retention time. The cryotrap was cooled by liquid carbon dioxide.

4. Mass Spectrometry (Example 5)

For mass spectrometric detection, the second column outlet flow was split between the second FID and an Ion Trap Detector (ITD 800, Finnigan MAT, San Jose, USA), owing to a Gerstel cross. The ITD transfer line (deactivated capillary, 0.45 m×0.25 mm) was heated to 250° C. (flow rate=1 mL.min$^{-1}$). A make-up of helium (1 mL.min−1) was added via this cross. The mass spectra were acquired under a 70 eV ionization potential. The range of masses acquired was 33<m/z<320 atomic mass units (amu). Compounds were identified by comparison of experimental data with those of Firmenich's internal data bank and by comparison of their retention time with those of authentic samples.

5. Sniffing Procedure

MDGC-Olfactometry (Example 6)

For the olfactometric detection, the second column outlet flow was split into two parts via a fused silica "Y" connector and directed to the second FID and to a thermostated transfer line (1 m×0.25 mm, Supelco) maintained at 200° C. The line was ended by a Dewar-type sniff port (silver coated double jacketed glass port under vacuum) to isolate the panelist's nose from the hot parts of the transfer line. A panel of 7 assessors was selected (4 men and 3 women aged 25 to 55 years). All of them regularly participated in sniffing sessions. During the 10 minutes session, they were asked to freely describe the aroma eluted from the second column. The start- and end-times of olfactive peaks and odor descriptions were noted. The seven individual aromagrams were averaged according to the detection frequency method published by Pollien et al. in *J.Agric.Food Chem.* 1997, 45, 2630-2637.

Olfactometric Characterization of Linalool Enantiomers (Example 9)

For the olfactometric characterization of enantiomers, the outlet of the cryotrap was directly connected to the FID and to the same sniff port as described above via a fused silica "Y" connector. The panelist was a perfumer. The start- and end-times of olfactive peaks and odor descriptions were noted. The experiment has been repeated three times.

6. Data Processing

Height, half-height width and resolution of peaks were calculated by the Galaxie Chromatography Data System software (Varian-JMBS). The resolution between two successive peaks was calculated according to the following formula:

$$Rs = 1.18 \times \frac{Rt_2 - Rt_1}{\omega_2 + \omega_1}$$

$Rt_1$ and $Rt_2$ represent the first and second peak retention time, respectively; $\omega_1$ and $\omega_2$ are the half height widths of the first and the second peaks, respectively.

Example 1

Manually Operated Interface

A very simple cryo-control was achieved by passing two strands of a column loop into a T-shape stainless-steel tube as represented in FIG. 2. The liquid $CO_2$ was admitted into the third branch of the T. The displacement of the T along the two strands of the column was achieved manually from the oven outside, with a rod attached to the T. Both columns were connected together using a zero-dead volume crosspiece. This latter was connected to a flame ionization detector via a deactivated capillary and to a pressure controller.

Figure 6:
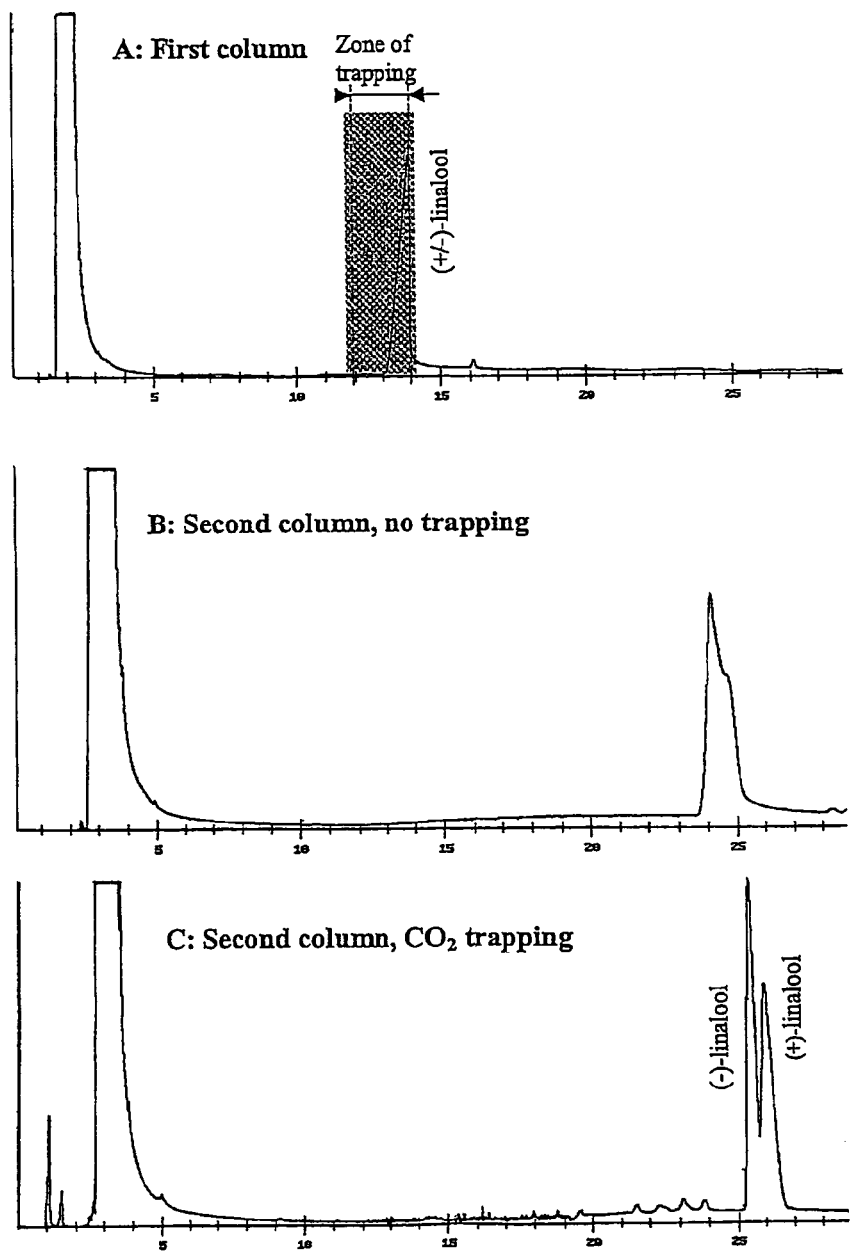
FIG. 6 shows a gas chromatograph trace of linalol under the analysis conditions described in Example 1. The temperature modulation means was manually operated. The first column was a SPB1, 30 m×0.25 mm×1.0 µm and the second a DB-WAX 30 m×0.25 mm×0.25 µm. Both detector means were FID.

Linalool enantiomers are known to be well separated using a 2,6-di-O-methyl-3-O-pentyl-β-cyclodextrin column. As a preliminary test, the racemate was injected into the MDGC in the configuration of FIG. 4, without cryo-trapping. Enantiomers were not separated (FIG. 6B). In a second experiment, the linalool peak eluting from the first column (FIG. 6A) was trapped between 12 and 14 min and then transferred to the chiral column according to the procedure of FIG. 4. Owing to the peak re-focusing provided by the cryo-control of the interface, enantiomers were resolved (FIG. 6C). In the three chromatograms, the elution time in the second column time was #11 min. The apparent later elution of linalool in C is due to the peak trapping in the interface and re-injection at 15 min.

Figure 7:
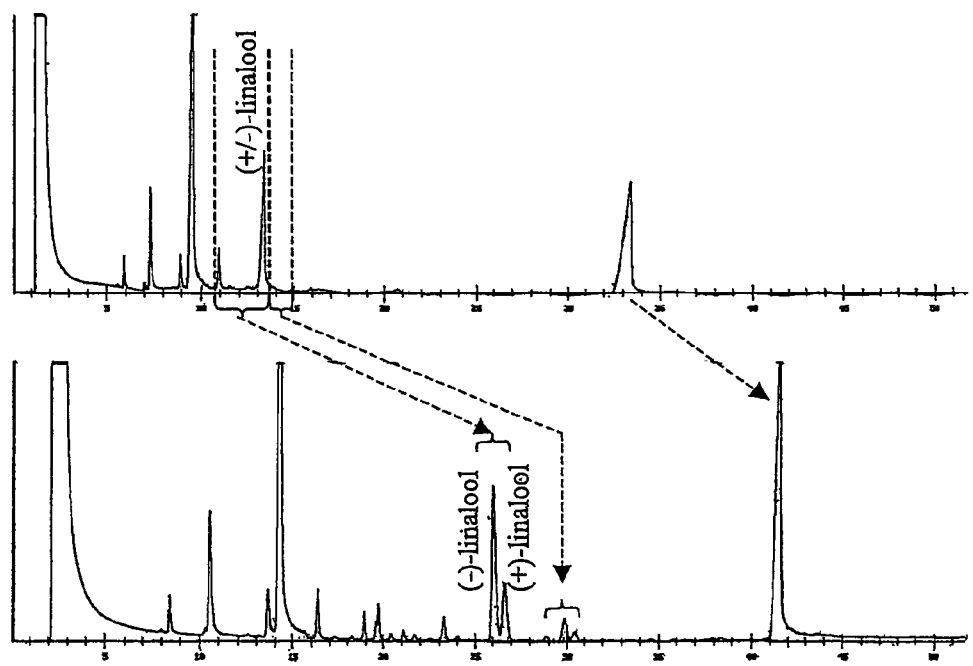
FIG. 7 shows a gas chromatograph trace of linalol in an adulterated bergamot essential oil under the analysis conditions described in Example 1. The temperature modulation means was manually operated. The first column was a SPB1, 30 m×0.25 mm×1.0 µm and the second a DB-WAX 30 m×0.25 mm×0.25 µm. Both detector means were FID.

A commercial bergamot essential oil was injected under the same conditions. The linalool peak indicated a significant proportion of the (+) isomer (FIG. 7), whereas, in an authentic bergamot pressed oil it should be in the range of 0.5% (H. Casabianca. et al. in *J. High Resol. Chromatogr.* 1998, 21, 107-112). This fact suggests that the commercial bergamot essential oil might have been diluted with some racemic linalool.

Example 2

Figure 8:
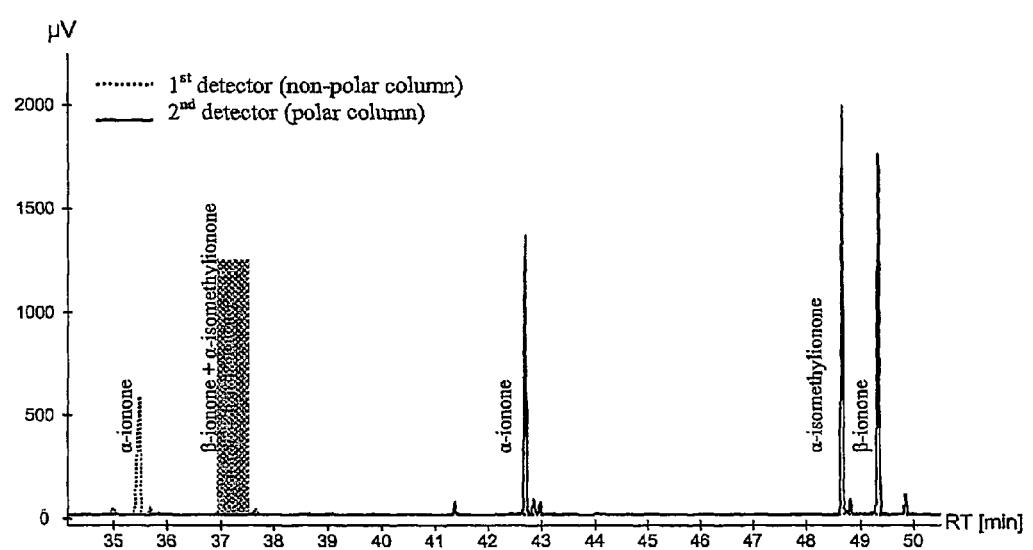
FIG. 8 shows a gas chromatograph trace depicting the separation of ionones under the conditions described in Example 2. The gray tint zone corresponds to the ionones peak transferred to the second column to be completely resolved thanks to the double-cool strand according to the invention. The temperature modulation means was automatically operated. The first column was a SPB1, 30 m×0.25 mm×1.0 µm and the second a DB-WAX 30 m×0.25 mm×0.25 µm. Both detector means were FID.

Remote-Controlled Hyphenation of a Non-Polar Column to a Polar Second Column (FIG. 8)

α-Ionone and β-ionone are often used in a same perfumery formula, such as violet-like fragrances, but they sometimes contain traces of α-isomethylionone, a suspected allergen. The separation of α-isomethylionone, α-ionone and β-ionone by either a single non-polar column (PDMS type), or a single polar column (carbowax-type) typically exemplifies the limitation of monodimensional-GC. α-Isomethylionone co-elutes with β- or α-ionone on non-polar column, and on polar column, respectively. Since all three compounds are structurally related, abundant MS ions for α-isomethylionone are not strictly characteristic of this compound to allow a peak deconvolution.

The MDGC apparatus of the invention however was able to resolve the target component from both peaks that were observed to interfere when using a single-column analysis.

A commercial blend of ionones was injected into the MDGC equipped with a non-polar first column coupled to a polar second column (Table 1). After the first column, α-isomethylionone was separated from α-ionone, but co-eluted with β-ionone (dotted line, FIG. 8). After a controlled transfer owing to the double cool-strand interface, it was clearly separated from α- and β-ionone (solid line, FIG. 8).

Table 2 summarizes the different trapping events. The peakheight increase observed in FIG. 8 will be discussed in the section "Efficiency and sensitivity improvement".

TABLE 2

Cryotrapping events

| Position of the cryotrap | Time (min) |
|---|---|
| Waiting position (see FIG. 5.1) | 36.00 |
| Trapping of target peaks (see FIG. 5.2) | 36.80 |
| Waiting position (see FIG. 5.3) | 37.20 |
| Pre-injection (see FIG. 5.4) | 38.00 |
| Waiting position (see FIG. 5.5) | 38.50 |
| Injection (see FIG. 5.6) | 44.00 |

Example 3

Multiple Heart-Cuts with a Remote-Controlled Interface

Prior known MDGC instruments, based on a valve or a pneumatic switching, allow to perform several heart-cuts during a single run, to further separate in the second column several groups of peaks co-eluted in the first column. The following example demonstrates that such a multiple transfer is also feasible with a double cool-strand interface.

Figure 9:
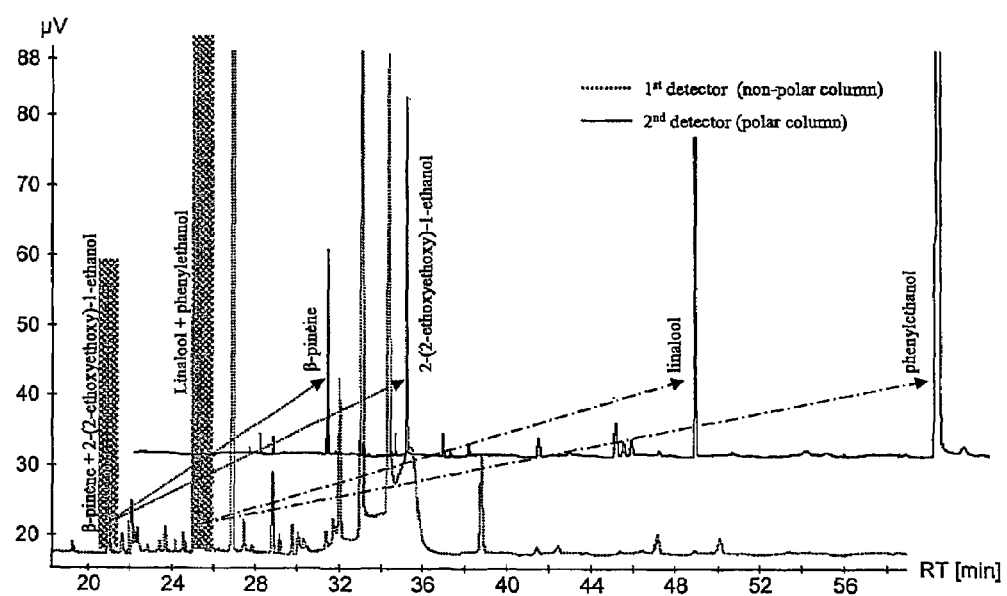
FIG. 9 shows a gas chromatograph trace of mixture of jasmine and hyacinth essential oils according to Example 3. The grey tint zones correspond to the peaks cryotrapped according to the invention to give the separated peaks depicted on the upper spectrum. The temperature modulation means was automatically operated. The first column was a SPB1, 30 m×0.25 mm×1.0 µm and the second a DB-WAX 30 m×0.25 mm×0.25 µm. Both detector means were FID.

A blend of jasmine and hyacinth essential oils was injected under the same chromatographic conditions as in Example 2. This blend exhibited co-elutions and overlaps using a non-polar column (β-pinene and 2-(2-ethoxyethoxy)-1-ethanol at 20.91 min, linalool and phenylethanol at 25.19 min, see FIG. 9). Two trapping/release sequences were achieved in the same run, according to Table 3. Those four peaks were eluted in a free zone of the second column, with an excellent resolution.

In such a case, the invention's interface ability to trap separately two closely eluted peaks is only limited by the speed of the peak transfer from the trapping to the injection strand. This depends principally on the analyte velocity in the loop, which is approximately the same as the velocity of the carrier gas. In the previous experiment for instance, the average velocity of the carrier gas was 30 cm.s$^{-1}$, meaning that the 25 cm of the capillary between both cool strand were crossed in 830 ms. The cryogenic trap motion and the column re-heating time were negligible compared to this step, because the cryogenic trap can move away from the cooled zone in less than 10 ms, while the cooled column heats up to the prevailing oven temperature within 10-15 ms (R. M. Kinghorn et al. in *J. High Resol. Chromatogr.* 2000, 23, 245-252). Even if these observations correspond to a single strand passing through the cryotrap, the order of magnitude of these times were assumed to remain identical for a double strand in the cryotrap. Experimentally, we observed that the retention time difference of two target peaks must exceed 1 second to allow their separate trapping.

TABLE 3

Table of time-events controlling the transfer of analytes in the two cool strands

| Time (min) | 1$^{st}$ strand | 2$^{nd}$ strand |
|---|---|---|
| 19.00 | Retention of peaks preceding the 1$^{st}$ target zone | |
| 20.75-21.70 | Retention then transfer of the 1$^{st}$ target zone (β-pinene and 2-(2-ethoxyethoxy)-1-ethanol) into the second strand | Retention then injection of peaks eluting before the 1$^{st}$ target zone |
| 21.70-24.75 | Retention then transfer of peaks eluting between both target zones into the second strand | Retention then injection of β-pinene and 2-(2-ethoxyethoxy)-1-ethanol into the second column |
| 24.75-26.20 | Retention then transfer of the 2$^{nd}$ target zone (linalool and phenylethanol) into the second strand | Retention then injection of peaks eluting between both target zones into the second column |
| 26.20-40.00 | Retention then transfer of peaks following the 2$^{nd}$ target zone into the second strand | Retention then injection of linalool and phenylethanol into the second column |

Example 4

Chiral Resolution in a Complex Mixture

Figure 10:
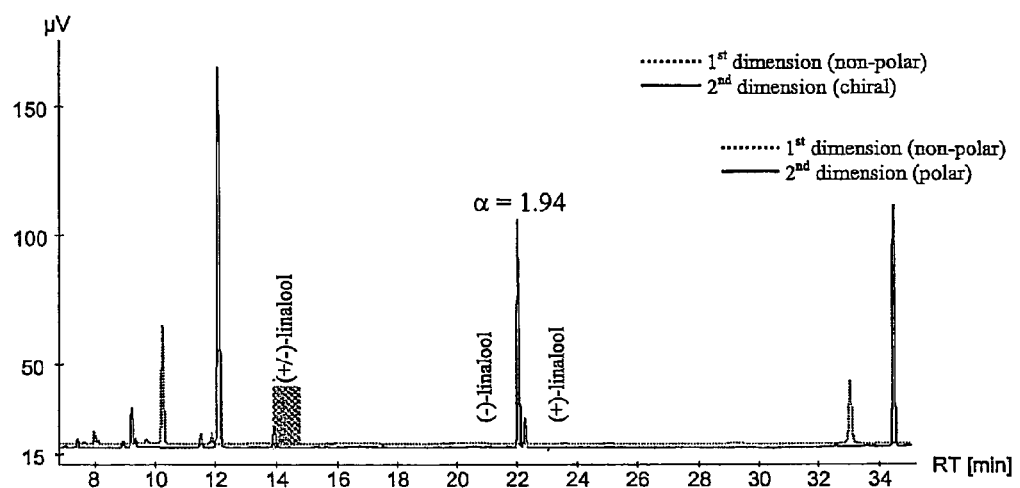
FIG. 10 shows a gas chromatograph trace resulting from MDGC-chiral analysis of linalol in adulterated bergamot oil, under the conditions described in Example 4. The grey tint zone corresponds to the cryotrapping zone of interest providing the resolved profile represented in full trace. The temperature modulation means was automatically operated. The first column was a SPB1, 30 m×0.25 mm×1.0 µm and the second a Megadex DMPβ 10 m×0.25 mm×0.25 µm. Both detector means were FID.

Natural products often contain chiral compounds the enantiomeric purity of which depends on their origin. Determining the enantiomeric ratios is a useful way to characterise the sample origin and a possible adulteration. Because of the relative complexity of natural oils, chiral compounds often require to be isolated from the others owing to a first non-chiral column, prior to their resolution in the chiral column of a MGGC system. A bergamot essential oil was injected in the MDGC with a non-polar column as first dimension connected to a chiral column as the second dimension (2,6-di-O-methyl-β-cyclodextrin, Table 1). The linalool re-injection in a free peak zone of the second column allowed a baseline resolution (α=1.94, FIG. 10), and an accurate determination of enantiomeric proportions (15/100, +/−). These values are far from the expected proportions in natural bergamot (0.5/100) (H. Casabianca et al. in *J. High Resol. Chromatogr.* 1998, 21, 107-112). This suggests an adulteration with some racemate addition. The same result had been observed with the apparatus of the invention comprising a manually operated. concentration/cooling zone (see Example 1).

Example 5

Hyphenation to Slow Detectors MDGC/MS

As both columns are operated under classical flow conditions, detectors with low sampling rates such as a quadrupole MS, an ion-trap MS may be used in the apparatus of the invention, in contrast to known comprehensive GC where fast detectors are required.

Figure 11:
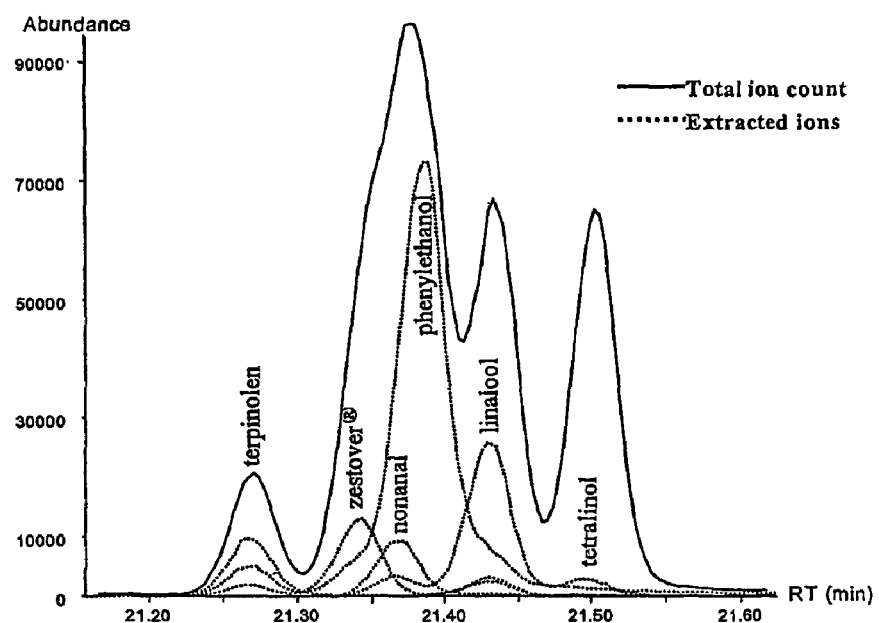
FIG. 11 shows gas chromatograph traces of the complex fragrance mixture cited in Examples 5 and 6.
Figure 11:
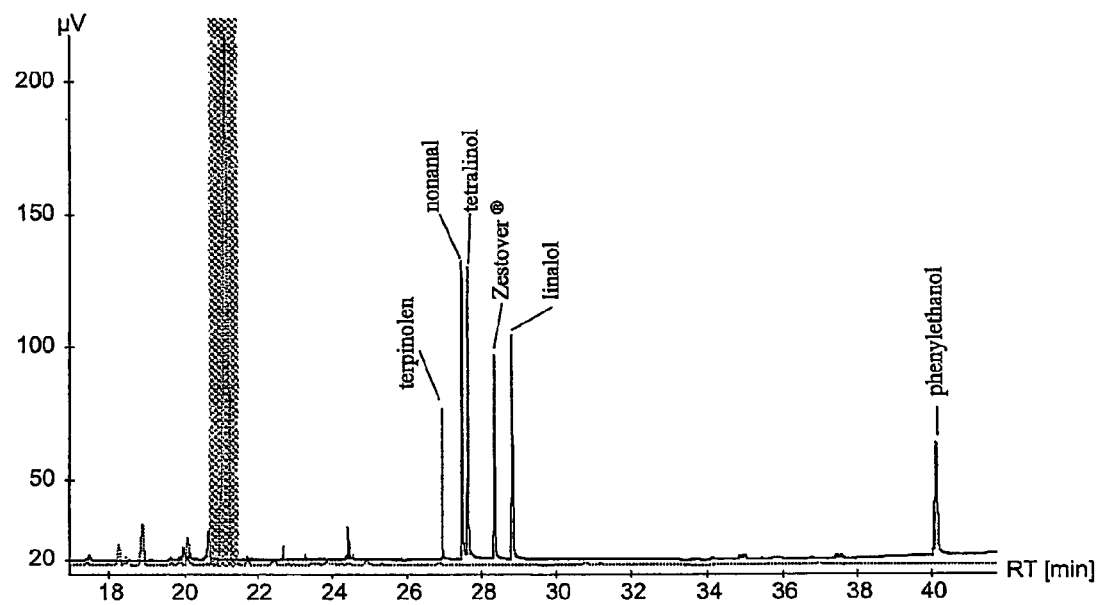

A quadrupole mass spectrometer was coupled to the MDGC system, after the second column. To test this configuration, a fragrance model mixture containing 6 compounds eluting at the same time on the first dimension was injected (terpinolene, nonanal, tetrahydrolinalool, Zestover®, linalool and phenylethanol, see FIG. 11a).

The fragrance model mixture was injected in the MDGC-MS system equipped with the double-strand cooling interface. Co-eluted compounds (20.90-21.50 min) were cryotrapped (gray-tint zone in FIG. 11b) and re-injected in the second column in a peak-free zone. All constituents were fully resolved (FIG. 11b), and unambiguously identified by the ion-trap MS (Table 6, Example 7).

Example 6

Hyphenation to Slow Detectors MDGC/Olfactometry

Figure 12:
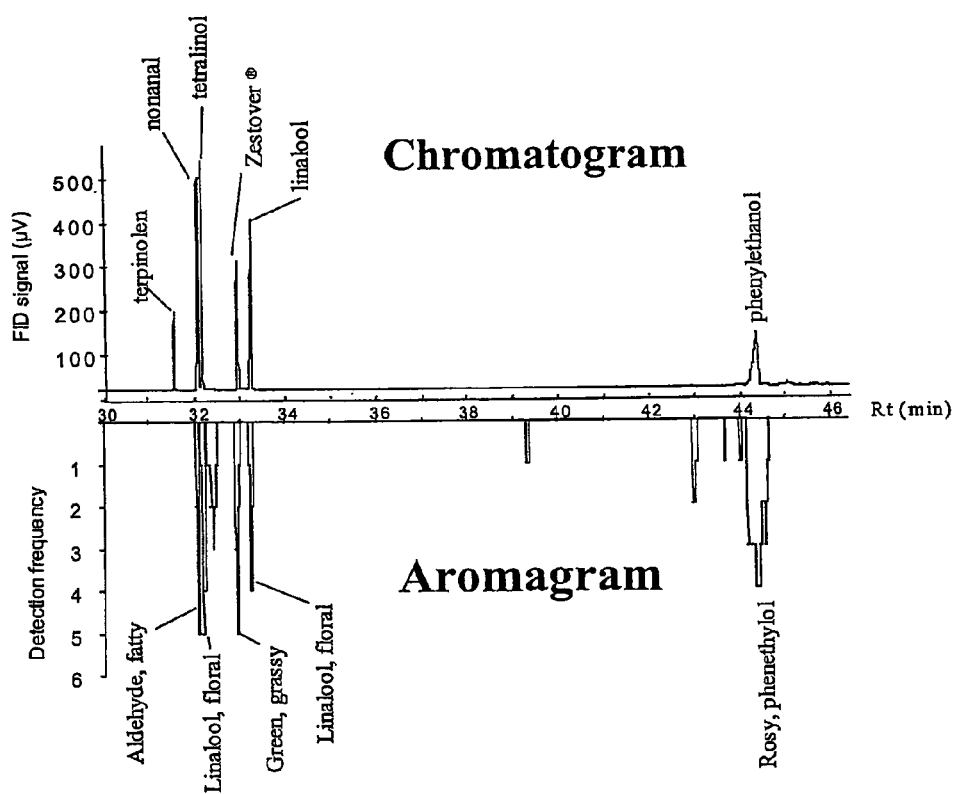
FIG. 12 was the MDGC analysis of the fragrance model. The temperature modulation means was automatically operated. The first column was a SPB1, 30 m×0.25 mm×1.0 µm and the second a DB-WAX 30 m×0.25 mm×0.25 µm. The first detector means was a FID (upper trace) whereas a FID and an olfactometric detector constituted the second detectors means (lower trace).

Another important and powerful slow-rate detector is the human nose. It is particularly employed in the field of flavor, fragrance and off-odor analysis. Eluting peaks have to be intense enough to be well perceived, and pure enough to allow evaluation by the panelist assigning them via the appropriate olfaction descriptors. A sniff port was connected at the end of the second column, instead of the mass spectrometer (chromatographic conditions are summarized in Table 1). The same model fragrance mixture as in Example 5 was injected, and 7 different evaluators smelled the odorants eluting from the second column and described them using a free vocabulary. The seven individual aromagrams were averaged and the resulting profile was compared to the FID signal (FIG. 12). All peaks were baseline separated and were significantly detected. Their descriptors perfectly fitted those from the literature (Table 4).

TABLE 4

Comparison between literature descriptors and the panelists' descriptors of eluting odorants

| Compound | Literature descriptors * | Panel descriptors |
|---|---|---|
| Terpinolen | Sweet-piney, oily, pleasant | Not perceived |
| Nonanal | Fatty-floral, waxy | Aldehydes, fatty |
| Tetrahydrolinalool | floral, linalool, green | Linalool, floral |
| Zestover ® | Sweet-green, leafy | Green, grassy |
| Linalool | Fresh, floral-woody, faintly citrus | Linalool, floral |
| Phenylethanol | Rosy, floral, green | Rosy, phenylethanlol |

* S. Arcander, Perfume and flavor chemicals, 1ed.; Maria G. Arctander, Las Vegas, Nevada, USA, 1969.

Example 7

Efficiency and Sensitivity Improvement of the Invention's Apparatus

Cryo-trapping analytes in a capillary is known to re-focus them. This improves the resolution and height of chromatographic peaks, thus increasing the sensitivity of the detection of traces in complex mixtures. The shape and the resolution of target peaks were compared with and without cryofocusing (i.e. either the two column in series, without trapping, or with a trapping/re-injection sequence, see Table 5) and this for the materials used in Examples 2, 4 and 5.

The poor chiral resolution of linalool in the absence of cryofusing did not allow the calculation of its areas, heights and half-height widths under these conditions.

As illustrated by the identical peak areas with or without trapping, cryofocusing and re-injection did not alter the quantity of detected analytes (Table 5). As a general observation, the heights and the resolution of targeted peaks were increased by a factor of 2-4, while the half-height width was reduced by a factor of 2-7, leading to an improved sensitivity for those compounds. As a consequence, this improvement in peak shape resulted in a better identification when using an MS detector (Table 6).

TABLE 5 comparison of areas heights, half height widths and resolutions of peaks using MDGC without and with cryotrapping (plain and bold character, respectively)

| Compound | Area (µV.min) | Height (µV) | Half height width | Resolution[a] |
|---|---|---|---|---|
| *Ionones* | | | | |
| α-ionone | 55.2/51.2 | 568.8/1348.2 | 0.07/0.03 | —/— |
| α-isomethylionone | 83.3/79.1 | 1003.4/1967.9 | 0.07/0.04 | —/— |
| β-ionone | 88.6/80.2 | 926.6/1740.7 | 0.08/0.04 | 3.09/10.13 |
| *Resolution of linalool* | | | | |
| (−)-linalool | —/9.4 | —/122.1 | —/0.07 | —/— |
| (+)-linalool | —/4.1 | —/50.7 | —/0.09 | 0.80/1.38 |
| *Fragrance model mixture* | | | | |
| terpinolen | 1.2/0.9 | 15.5/56.3 | 0.07/0.01 | —/— |
| nonanal | 2.7/2.5 | 43.7/111.9 | 0.06/0.02 | 4.66/19.92 |
| tetrahydrolinalool | 2.8/2.6 | 48.5/109.9 | 0.05/0.02 | 2.11/4.73 |
| Zestover ® | 2.4/2.2 | 40.8/76.7 | 0.05/0.03 | 5.13/19.02 |
| linalool | 3.1/2.9 | 59.6/84.4 | 0.05/0.03 | 3.43/10.34 |
| phenylethanol | 3.0/2.9 | 59.6/42.8 | 0.05/0.06 | —/— |

[a] Resolution between the previous and the target peak

TABLE 6

Comparison of the MS identification quality of
the constituents of a fragrance model mixture
injected in a MDGC, with and without trapping

| | Match quality without trapping | Match quality with trapping |
|---|---|---|
| Terpinolene | 97 | 98 |
| Zestover ® | Wrong identification | 98 |
| Nonanal | Wrong identification | 98 |
| Phenylethanol | 46 | 96 |
| Linalool | 87 | 94 |
| Tetrahydrolinol | 78 | 96 |

Example 8

Use of a Single Oven to Operate Both Columns at Different Temperatures

Figure 13:
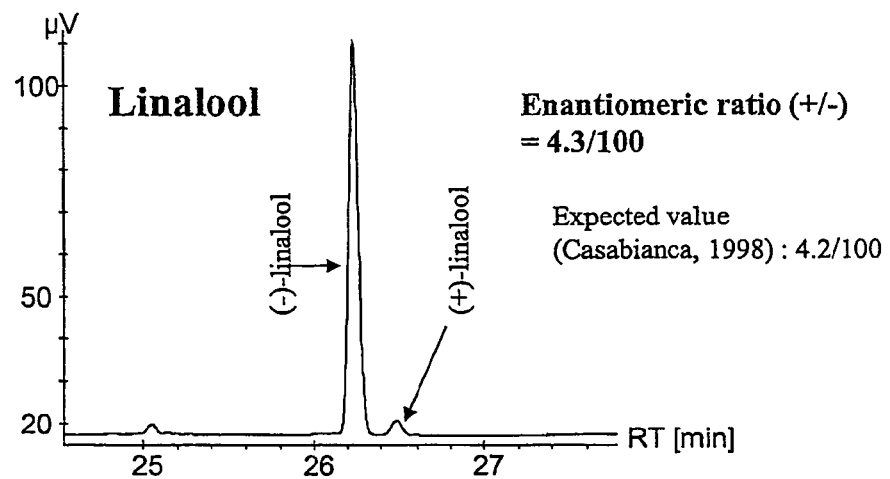
FIG. 13 show the chromatogram traces resulting of the resolution during the same analysis of the two main chiral compounds of lavender oil. The temperature modulation means was automatically operated. The first column was a CP-Sil5CB 30 m×0.32 mm×1.0 µm and the second a Megadex DETTBSβ 25 m×0.25 mm×0.25 µm. Both detector means were FID.
Figure 13:
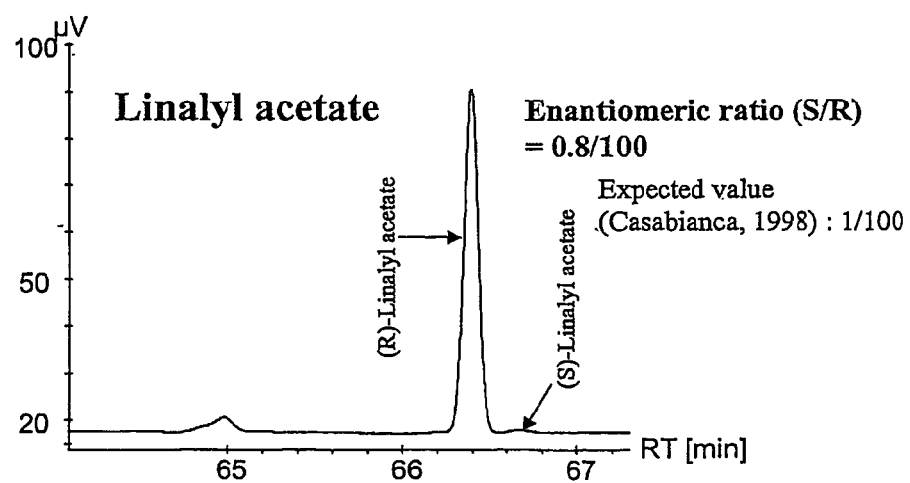

Sometimes the temperature elution of a given compound from the first dimension is too high for its resolution in the second dimension. This is especially the case with a chiral second dimension in which the enantiomer resolution is very temperature-dependent (V. Schurig, *Journal of Chromatography A* 2001, 906, 275-299). This situation requires two separate ovens to operate both columns at different temperature. Using the apparatus of the invention, due to the controlled trapping of the target compound in the interface, the oven can be rapidly cooled down to the initial temperature required by the second column before re-injecting the analytes in the second column. To illustrate this capability, the two main chiral constituents of lavender oil, linalool and linalyl acetate, were resolved within the same analysis. The controlled cryotrapping of these compounds allowed the adaptation of the chromatographic conditions (cooling of the oven before re-injection in the second dimension) to achieve the best resolution of those racemates. Both compounds were resolved independently from each other during the same analysis: linalool was resolved using a isothermal conditions whereas linalyl acetate has been resolved under slow temperature ramp (see Table 7). The enantiomeric ratios for both compounds suggest that this lavender oil was an authentic natural essential oil (FIG. 13).

TABLE 7

Table of time-events controlling the transfer of analytes
in the two cool strands for the resolution of linalool
and linalyl acetate in lavender oil.

| Time (min) | $1^{st}$ strand | $2^{nd}$ strand | Oven |
|---|---|---|---|
| 10.00 | Retention of peaks preceding the $1^{st}$ target zone (linalool) | | Temperature increase (8° C./min) to 165° C. |
| 16.10-16.80 | Retention then transfer of the $1^{st}$ target zone (linalool) into the second strand | Retention then injection of peaks eluting before the $1^{st}$ target zone | Isotherm at 165° C. then temperature decrease (25° C./min) to 120° C. |
| 16.80-24.80 | Retention then transfer of peaks eluting between both target zones into the second strand | Retention then injection of linalool into the second column | Isotherm at 120° C. |
| 24.80-25.85 | Retention then transfer of the $2^{nd}$ target zone (linalyl acetate) into the second strand | Retention then injection of peaks eluting between both target zones into the second column | Temperature decrease (25° C./min) to 50° C. |
| 25.85-30.00 | Retention then transfer of peaks following the $2^{nd}$ target zone into the second strand | Retention then injection of linalyl acetate into the second column | Temperature increase (2° C./min) to 150° C. |

Example 9

Figure 14:
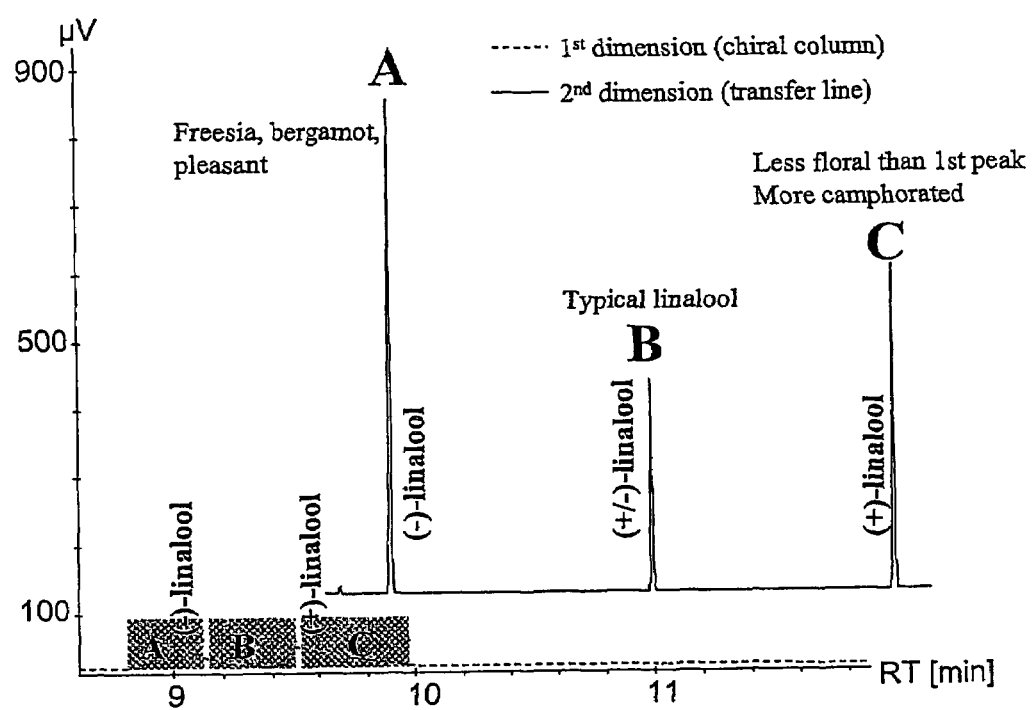
FIG. 14 corresponds to the chromatogram traces of the resolution and improvement in the separation of the enantiomers of linalool for olfactometric characterization. The temperature modulation means was automatically operated. The first column was a Megadex DMPβ 10 m×0.25 mm×0.25 µm and the second a short transfer line. The first detector means was a FID whereas the second was an olfactometric detector.

Improvement of the Chiral Resolution for the Olfactometric Characterization of Linalool Enantiomers As many chiral compounds exhibits different olfactive sensations from one enantiomer to another, the olfactive contribution of chiral compounds to the global odour may depend on their enantiomeric ratio. Even with the most appropriate chiral column, the resolution achieved between two enantiomers is notably insufficient to allow a good characterization by a panelist. By combining a chiral column as the first dimension and a simple transfer line connected to a sniff port as the second dimension, it is possible to increase the time interval between enantiomers by stoping the second enantiomer while the first one is eluted and evaluated. A solution of racemic linalool was injected in the MDGC with a chiral column as the first dimension. The chiral phase was a 2,6-di-O-methyl-β-cyclodextrin, well known for its ability to separate linalool enantiomers. Three target zones were defined as follows: two thirds of the first peak (gray tint zone A, FIG. 13), then the last third of the first peak plus the first third of the second (gray tint zone B, FIG. 13), and lastly the last two thirds of the second peak (gray tint zone C, FIG. 14). To achieve the maximum comfort for the panelist, the retention time difference between each peak was fixed to one minute. Both enantiomers could be easily evaluated during the same run. Such a result couldn't be obtained with other techniques.

What is claimed is:

1. An apparatus for the concentration or analysis of chemical components of a chemical sample that includes a mixture of such components, the apparatus comprising:
   separation means for separating the components of the sample into a chemical sample fluid stream;
   conduit means equipped with temperature modulation means, with the conduit means having a receiving port for receiving the chemical sample fluid stream from the separation means and an outlet port for expelling the chemical sample fluid stream, the ports being in fluid communication with each other to allow movement of the fluid stream from the inlet port towards the outlet port, with the temperature modulation means being capable of cooling one or more portions of the conduit means and the portion(s) of the chemical sample fluid stream therein, so as to cause at least decrease of the movement of the portion(s) of the fluid stream, and of allowing warming up of the portion(s) of the chemical sample fluid stream after the cooling so as to resume movement thereof in the conduit means, wherein:

a) the conduit means and the temperature modulation means are arranged in such a way as to allow a selected component of the chemical sample fluid stream to be cooled at least twice before expulsion thereof through the outlet port; and b) detector means are provided up-stream of the first cooling portion of the conduit means to detect peak or band information to identify the selected component of the fluid stream; and c) a computer is provided to operate the thermal modulation means to cool the selected component based on the detected peak or band information so as to allow control of the residence time of the chemical sample fluid stream in the cooled portion or portions of the conduit means for analysis thereof.

2. The apparatus according to claim 1, wherein the conduit means are in the form of a loop comprising a double strand portion, with a single temperature modulator being arranged in the double strand portion in such a way as to allow simultaneous or non-simultaneous first and second coolings of the chemical sample fluid stream before expulsion thereof through the outlet port.

3. The apparatus according to claim 2 which comprises a second temperature modulation means.

4. The apparatus according to claim 1, wherein the temperature modulation means are moveable relative to the conduit means.

5. The apparatus device according claim 1, wherein the temperature modulation means are moveable cooling means or cryotraps.

6. The apparatus according to claim 5, wherein the cooling means has a length of between 0.1 mm and 500 mm.

7. The apparatus according to claim 5, wherein the movement of the cooling means is pre-programmed and controlled by the computer.

8. The apparatus according to claim 5, wherein the cooling means can cool the chemical sample to a temperature between $-150°$ C. and $100°$ C.

9. The apparatus according to claim 5, wherein at least part of the portion of the conduit not subjected to the cooling means is subjected to a heating means.

10. The apparatus according to claim 1, wherein the conduit means is incorporated into or associated with the separation means, and the separation means is a chromatographic column or spectroscopic, separation or detection apparatus.

11. The apparatus according to claim 10, wherein the conduit is a tube which forms part of the chromatographic column.

12. The apparatus according to claim 11, wherein the chromatographic column is a packed gas chromatography column, a wide-bore gas chromatography column or a capillary gas chromatography column.

13. The apparatus according to claim 1, wherein the conduit comprises a first section, a connecting section and a second section wherein the cooling means is moveable along the connecting section.

14. The apparatus according to claim 13, wherein the connecting section is a concentrating section and the first and second sections are separating sections which each comprise a housing which has a variable temperature of less than $400°$ C.

15. The apparatus according to claim 1, wherein the detector means includes a first flame ionization detector located in the conduit means upstream of the temperature modulation means and a second flame ionization detector located downstream of the temperature modulation means.

16. A method of concentrating or analyzing chemical components of a chemical sample that includes a mixture of such components, which method comprises:

a) separating the components of the sample into a chemical sample fluid stream and directing the chemical sample and fluid stream into a conduit and allowing the components of the chemical sample fluid stream to travel through the conduit;

b) cooling a first portion of the conduit to a predetermined temperature and maintaining the predetermined temperature using thermal modulation means;

c) accumulating within the cooled portion of the conduit for a predetermined period of time a portion of the chemical sample fluid stream, thus forming a first concentrated band;

d) changing the temperature of the cooled portion of the conduit to allow warming thereof and release the first concentrated band of the chemical sample fluid stream within the first cooling portion of the conduit, and e) repeating steps c) to d) as many times as desired to obtain as many subsequent concentrated bands of such components as the number of times these steps are repeated, wherein:

i) prior to step c) the chemical sample is analyzed to identify a component of the chemical sample fluid stream to be thus concentrated; and (ii) each concentrated band is subjected to at least a second concentration step via at least a second cooling and warming sequence.

17. The method according to claim 16, wherein the conduit comprises a carrier fluid.

18. The method according to claim 16, wherein the chemical sample is analyzed in detector means.

19. The method according to of claim 18, wherein the detector means includes a first flame ionization detector located in the conduit upstream of cooling and a second flame ionization detector located downstream of cooling.

* * * * *

UNITED STATES PATENT AND TRADEMARK OFFICE
CERTIFICATE OF CORRECTION

PATENT NO. : 7,490,506 B2
APPLICATION NO. : 11/582919
DATED : February 17, 2009
INVENTOR(S) : Chaintreau et al.

It is certified that error appears in the above-identified patent and that said Letters Patent is hereby corrected as shown below:

Column 24:
Line 50 (claim 19, line 1), before "claim" delete "of".

Signed and Sealed this

Twenty-eighth Day of April, 2009

JOHN DOLL
*Acting Director of the United States Patent and Trademark Office*